United States Patent
Kalchauer et al.

(12)

(10) Patent No.: US 6,211,394 B1
(45) Date of Patent: Apr. 3, 2001

(54) PROCESS FOR THE PREPARATION OF ORGANOCHLOROSILANES

(75) Inventors: Wilfried Kalchauer, Burghausen; Herbert Straussberger, Mehring/Öd; Willibald Streckel, Mehring/Öd; Jochen Gross, Mehring/Öd, all of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/625,811

(22) Filed: Jul. 26, 2000

(30) Foreign Application Priority Data

Aug. 11, 1999 (DE) ................................. 199 37 908

(51) Int. Cl.$^7$ ...................................................... C07F 7/16
(52) U.S. Cl. ............................................................. 556/472
(58) Field of Search ............................................. 556/472

(56) References Cited

U.S. PATENT DOCUMENTS

| 4,504,596 | 3/1985 | Schoepe et al. . |
| 5,777,146 | 7/1998 | Straussberger . |
| 5,817,855 | * 10/1998 | Langner et al. ..................... 556/472 |
| 5,876,609 | * 3/1999 | White et al. .......................... 556/472 |
| 6,057,469 | * 5/2000 | Margaria et al. .................... 556/472 |

FOREIGN PATENT DOCUMENTS

| 197 52 261 C1 | 1/1999 | (DE) . |

OTHER PUBLICATIONS

K.M. Lewis and D.G. Rethwisch, "Catalyzed Direct Reactions of Silicon", Studies in Organic Chemistry 49, 1993.
G. Rtyl, H. Knözinger, and J. Weitkamp, "Handbook of Heterogeneous Catalysis", vol. 4, Chapter 2, 1965.
Walter Noll, "Chemistry and Technology of Silicones", Academic Press, Inc., 1968, p. 29.
Derwent Abstract Corresponding To DE 197 52 261 C (AN 1999–082687).
International Search Report—Oct. 5, 2000.

* cited by examiner

*Primary Examiner*—Paul F. Shaver
(74) *Attorney, Agent, or Firm*—Brooks & Kushman P.C.

(57) ABSTRACT

The invention relates to a continuous process for the direct synthesis of methylchlorosilanes by reacting chloromethane with a catalyst composition comprising silicon, zinc promoter and copper catalyst which is selected from a) copper oxide,
b) mixtures of at least 80% by weight of copper oxide and copper(I) chloride,
c) copper(I) chloride and
d) mixtures of at least 80% by weight of copper(I) chloride and copper oxide, where copper catalysts a), b), c) or d) are employed alternately in such a way that copper catalyst a) or b) is followed by c) or d), or copper catalyst c) or d) is followed by copper catalyst a) or b).

7 Claims, No Drawings

US 6,211,394 B1

PROCESS FOR THE PREPARATION OF ORGANOCHLOROSILANES

TECHNICAL FIELD

The invention relates to a continuous process for the direct synthesis of methylchlorosilanes by reacting chloromethane with a catalyst composition comprising silicon and copper catalyst.

BACKGROUND ART

In the Müller-Rochow direct synthesis of methylchlorosilanes, methychloride is reacted with silicon in the presence of a copper catalyst and suitable promoters to give methylchlorosilanes. In addition to the highest possible productivity based on the amount of silanes formed per time unit and reaction volume, the highest possible selectivity, based on the target product dimethyldichlorosilane, is also required. Dimethyldichlorosilane is required, for example, for the preparation of linear polysiloxanes.

The direct synthesis can be carried out batchwise or continuously, with the continuous version being preferred in industrial production. The continuous direct synthesis is carried out in fluidized-bed reactors in which methyl chloride is employed simultaneously as fluidization medium and reactant. The silicon required is firstly ground to a powder having a particle size of at most 700 μm, and mixed with copper catalyst and promoters to provide the catalyst composition.

In continuous operation of a reactor, the production rate, based on methylchlorosilanes, and the selectivity, based on the target product dimethyldichlorosilane, drop after a substantially stable production phase. For this reason, the production campaign must be terminated after a certain time. A production campaign therefore usually lasts from only a few days to several weeks.

After termination of a production campaign, the reactor is emptied, refilled with silicon, copper catalyst and promoters, and restored to the reaction conditions. After a certain induction phase, the formation of crude silane begins. This is followed by the start phase, i.e. the reaction initially proceeds with low selectivity and reactivity. The reactor then subsequently reaches the stable production phase again. It can be seen from this that the economic efficiency of the direct synthesis can be increased with constant selectivity by increasing the production rate.

The reactivity and selectivity in the direct synthesis are highly dependent on the catalysts and promoters employed. U.S. RE 33,452 describes, for example, a direct synthesis using a catalyst combination of the elements or compounds of copper, zinc and tin. The ratio of copper, zinc and tin to one another has a considerable effect on the process, in particular on the productivity and selectivity, while the form in which the catalysts are introduced into the catalyst composition, for example as metal, alloy or chemical compound, is of secondary importance.

In "Catalyzed Direct Reactions of Silicon", edited by K. M. Lewis and D. G. Rethwisch, Elsevier, 1993, Chapter 1 "Commercial Production of Silanes by the Direct Synthesis", B. Kanner, K. M. Lewis, page 12, various copper catalysts are described which are used in the process carried out on a large industrial scale. For example, it is shown that copper(I) chloride can be used as the only copper component, but a mixture of copper oxide and copper(I) chloride is sometimes also used. By use of such mixtures, the induction period is shortened and the reactivity is increased; the effect of these mixtures on the selectivity has not been reported.

In "Handbook of Heterogeneous Catalysis", edited by G. Ertl, H. Knözinger, J. Weitkamp; Volume 4, Wiley-VCH; Chapter 2 (Inorganic Reactions), 2.5 The Direct Process to Methylchlorosilane (Müller-Rochow Synthesis) by B. Pachaly, page 1788, it is stated that the advantage of copper oxide over CuCl in the large-scale industrial process is that the conversion of copper oxide into copper chloride which takes place in the reaction system is slower than the reaction of CuCl to $Cu_3Si$, which represents the actual reaction center. The steady-state concentration of CuCl is thus very low, less metallic copper is formed by the redox reaction of copper chloride with metallic silicon, and the undesired side reactions initiated by metallic copper, which reduce the selectivity, occur to a reduced extent. At the same time, the possibility of employing various mixtures of different copper catalysts is disclosed.

In "Chemistry and Technology of Silicones", W. Noll; Academic Press, 1968, page 29, it is stated that copper(I) chloride can be employed instead of metallic copper, but in this case the proportion of methyldichlorosilane increases, i.e. the selectivity drops.

The chemical nature of the copper catalyst employed in the catalyst system has a massive effect on the reactivity and selectivity. Copper(I) chloride gives very good reactivity, with the selectivity dropping greatly with advancing reaction time; copper oxide shows long-lasting good selectivity at the same time as moderate reactivity. If a mixture of copper oxide and copper chloride is employed as catalyst, the reaction behavior is determined by one of the two individual components, depending on the mixing ratio.

DISCLOSURE OF INVENTION

An object of the present invention was to provide a process for the direct synthesis of methylchlorosilanes by the Müller-Rochow method in which the productivity can be increased while retaining the dimethyldichlorosilane selectivity. This and other objects have been achieved by the process of the invention, in which catalyst compositions fed to the reactor are alternated.

BEST MODE FOR CARRYING OUT THE INVENTION

The invention relates to a continuous process for the direct synthesis of methylchlorosilanes by reacting chloromethane with a catalyst composition comprising silicon, zinc promoter, and a copper catalyst which is selected from a) copper oxide, b) mixtures of at least 80% by weight of copper oxide and copper(I) chloride, c) copper(I) chloride, and d) mixtures of at least 80% by weight of copper(I) chloride and copper oxide, where copper catalysts a), b), c) or d) are employed alternately in such a way that copper catalyst a) or b) is followed by copper catalyst c) or d), or copper catalyst c) or d) is followed by copper catalyst a) or b).

The present invention is based on the knowledge that phasewise alternation of the copper catalyst component from copper oxide to copper(I) chloride and vice versa retains the positive properties of the individual copper components, namely good reactivity of copper(I) chloride and long-lasting selectivity of copper oxide without the negative properties, namely moderate reactivity of copper oxide and drop in selectivity in the case of copper(I) chloride, occurring at the same time.

If, for example, the reaction in the process according to the invention is started with a catalyst composition comprising copper catalyst a) or b), the copper catalyst is changed to c) or d) as soon as the reaction is stable with respect to reactivity and selectivity, after which the reactivity rises very rapidly without the selectivity first being reduced. This catalyst mixture is retained until the selectivity begins to drop significantly. Copper catalyst a) or b) is subsequently restored, and the selectivity begins to rise again with retention of the reactivity. As soon as the selectivity has reached the desired high level and at the same time the reactivity begins to drop again, the copper component is changed back to copper catalyst c) or d). This operation can be repeated as often as desired during a reactor run time.

The reaction can also be started with a catalyst composition comprising copper catalyst c) or d). In this case, the copper catalyst is changed to copper catalyst a) or b) as soon as the selectivity drops significantly. The remainder of the procedure corresponds analogously to the procedure described above.

A catalyst change preferably takes place after from 1 to 1000 hours, in particular after from 5 to 200 hours.

The copper catalysts b) preferably comprise at least 90% by weight of copper oxide. The copper catalysts d) preferably comprise at least 90% by weight of copper(I) chloride.

The process is preferably carried out in a fluidized-bed reactor, preferably in the temperature range from 250° C. to 350° C., in particular from 270° C. to 320° C. The process is usually carried out at from the pressure of the ambient atmosphere (i.e. about 0.1 MPa) to 0.5 Mpa, since this requires the least effort, but higher pressures can also be used.

Further additives as described in the literature can also be added to the catalyst composition or the gas stream during the process. Preferably, though, no further additives are added.

The amount of gas stream is, in a preferred embodiment, selected in such a way that a fluidized bed of catalyst composition and gas is formed in the reactor. The mixture of silicon, catalysts and promoters is referred to as the catalyst composition. Unreacted chloromethane and the gaseous methylchlorosilanes leave the reactor. If desired, the entrained particles can be separated from the gas stream via one or more cyclones, large entrained particles of the catalyst composition being fed back into the reactor.

The crude silane is subsequently separated from residual dust components and unreacted chloromethane and fed to a distillation. Purified, unreacted chloromethane can be fed back into the reactor.

The catalyst composition is prepared by simply mixing the individual components at room temperature. Subsequent thermal treatment of the catalyst composition before introduction into the reactor is possible, but is not carried out in the preferred embodiment.

The process is carried out continuously. This means that the amount of silicon that has reacted and catalysts and promoters discharged with the reaction dust are continuously replenished, preferably as premixed catalyst composition.

In a preferred embodiment of the process according to the invention, silicon is employed in a particle size of less than 700 $\mu$m, most preferably in a particle size of less than 500 $\mu$m and greater than 20 $\mu$m. The silicon employed usually has a purity of >99%.

Copper oxide is employed in the process according to the invention in the form of copper(II) oxide, in the form of copper(I) oxide or as mixed oxides. In the case of mixed oxides of the general formula $CuO_x$, x has a value of from 0.5 to 1, preferably of at least 0.7. The copper oxides described can be prepared, for example, by the process described in U.S. Pat. No. 5,306,328, where the degree of oxidation can be set to a specific value through the drying temperature and the residence time at this temperature. The copper oxides can also contain a small amount of metallic copper. The copper metering rate is preferably selected in such a way that the catalyst composition, irrespective of whether copper catalysts a), b), c) or d) are employed, preferably comprises from 0.3 to 10% by weight, more preferably from 0.5 to 7% by weight, and most preferably from 0.8 to 5% by weight, calculated as metallic copper and based on the silicon employed.

In the process according to the invention, zinc is preferably employed in the form of metallic zinc, alternatively as an alloy with further promoters, or in the form of zinc oxide or zinc chloride. The amount of zinc employed is selected so that the catalyst composition preferably contains from 0.005 to 1.0% by weight of zinc, more preferably from 0.010 to 0.50% by weight of zinc, and most preferably from 0.015 to 0.35% by weight of zinc, calculated as metallic zinc and based on silicon.

Further promoters which can be employed are preferably phosphorus, cesium, barium, iron, more preferably tin or antimony, or combinations thereof.

In the process according to the invention, the promoters are preferably employed in the form of metals or alloys. The amount of promoters employed is selected so that the catalyst composition preferably contains from 5 to 100 ppm, more preferably from 10 to 80 ppm, and most preferably from 15 to 60 ppm of promoters, calculated as metallic promoters and based on silicon.

In the examples below, unless otherwise stated, a) all amounts are by weight;

b) all pressures are 0.10 MPa (abs.);

c) all temperatures are 20° C.

EXAMPLES

The following copper catalysts are employed in an industrial-scale fluidized-bed reactor (about 30 metric tons of catalyst composition) with continuous charging of catalyst composition, main cyclone with dust recycling and post-cyclone with dust discharge. The tests were made under comparable conditions (temperature, pressure, gas flow rate, silicon quality, promoters: Sn and $ZnCl_2$, etc.). The data given relate to the stable production phase.

Example 1 (not according to the invention)

CuO was prepared by the process described in U.S. Pat. No. 5,306,328. Over a period of 7 days, the selectivity and reactivity remained constant within a certain variation latitude in the rolling 8-hour mean at:

3.2 metric tons of crude silane per hour (+/−0.3)

85.2% by weight (+/−1.7%) of dimethyldichlorosilane in the crude silane. These results indicate that CuO produces long-lasting good selectivity at the same time as moderate reactivity.

Example 2

CuCl is commercially available from Faravelli Chemiehandelsges. mbH, Germany. The copper catalyst was changed from CuO to CuCl in the stable production phase in the running reactor, which was started with CuO (reactivity and selectivity as indicated in Example 1).

15 hours after the catalyst changeover, the following data were determined in the 8-hour mean:
   3.9 metric tons of crude silane per hour
   86.9% by weight of dimethyldichlorosilane in the crude silane;
72 hours after the catalyst changeover, the following data were determined in the 8-hour mean:
   4.5 metric tons of crude silane per hour
   81.0% by weight of dimethyldichlorosilane in the crude silane These results indicate that the selectivity drops drastically after a certain time on extended use of CuCl.

The catalyst was subsequently changed back from CuCl to CuO.

12 hours after the change, the following data were determined:
   4.5 metric tons of crude silane per hour
   83.8% by weight of dimethyldichlorosilane in the crude silane.
36 hours after the catalyst change, the following data were determined in the 8-hour mean:
   4.0 metric tons of crude silane per hour
   85.4% by weight of dimethyldichlorosilane in the crude silane.
96 hours after the catalyst change, the 8-hour means shown in Example 1 were obtained. The overall results indicate that CuCl produces very good reactivity with dropping moderate selectivity, and that a continuous catalyst change from CuO to CuCl and back enables high reactivity to be achieved at the same time as good selectivity.

Example 3

The procedure used was analogous to that of Example 2. In the constant production phase of a CuO catalyst composition, the selectivity in the 8-hour mean immediately before the catalyst change to CuCl was:
   86.9% by weight of dimethyldichlorosilane.
96 hours after the catalyst change and immediately before the recent change to CuO, the selectivity in the 8-hour mean was:
   83.4% by weight of dimethyldichlorosilane.
16 hours after the last catalyst change and immediately before the recent change to CuCl, the selectivity in the 8-hour mean was:
   86.5% by weight of dimethyldichlorosilane.
37 hours after the last catalyst change and immediately before the recent change to CuO, the selectivity in the 8-hour mean was:
   84.9% by weight of dimethyldichlorosilane.
17 hours after the last catalyst change and immediately before the recent catalyst change, the selectivity in the 8-hour mean was:
   86.8% by weight of dimethyldichlorosilane.

Example 4 (not according to the invention)

After Example 3, a mixture of CuO and CuCl in a weight ratio of 3:1 was employed in the next catalyst change; 12 hours after the change, the selectivity dropped back to 83.9% by weight of dimethyldichlorosilane. These results indicate that a mixture of CuCl and CuO which is outside the range of the invention do not result in the same beneficial effect as catalysts within the range.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A continuous process for the direct synthesis of methylchlorosilanes, comprising reacting chloromethane with catalyst compositions comprising silicon, zinc promoter and copper catalyst, said copper catalyst added to the reactor in a sequential manner, said copper catalyst selected from the group consisting of
   a) copper oxide,
   b) mixtures of at least 80% by weight of copper oxide and copper(I) chloride,
   c) copper(I) chloride and
   d) mixtures of at least 80% by weight of copper(I) chloride and copper oxide,
   wherein copper catalysts a), b), c) or d) are employed sequentially in such a way that copper catalyst a) or b) is followed by c) or d), or copper catalyst c) or d) is followed by copper catalyst a) or b).

2. The process of claim 1, where a catalyst change from one of a) through d) to another of a) through d) takes place after from 1 to 1000 hours.

3. The process of claim 1, in which further promoters are employed, at least one of these further promoters selected from the group consisting of phosphorus, cesium, barium, iron, tin and antimony.

4. The process of claim 2, in which further promoters are employed, at least one of these further promoters selected from the group consisting of phosphorus, cesium, barium, iron, tin and antimony.

5. The process of claim 1 wherein said sequential addition of catalyst mixtures is alternated throughout a portion of a production phase of said continuous process.

6. A process for extending the production phase of a continuous process for the direct synthesis of methylchlorosilanes by reacting chloromethane with silicon metal containing zinc promoter, copper catalyst, and optionally further promotors, said process comprising alternately adding to the reactor during at least said production phase, a catalyst composition rich in copper oxide relative to copper (I) chloride, and a catalyst composition rich in copper (I) chloride relative to copper oxide.

7. The process of claim 6, in which at least three alternating changes of catalyst occur.

* * * * *